United States Patent
Hsu et al.

(10) Patent No.: US 10,393,718 B2
(45) Date of Patent: Aug. 27, 2019

(54) MICRO-ELECTROMECHANICAL APPARATUS FOR THERMAL ENERGY CONTROL

(71) Applicant: Industrial Technology Research Institute, Hsinchu (TW)

(72) Inventors: Yu-Wen Hsu, Tainan (TW); Ying-Che Lo, Tainan (TW); Chao-Ta Huang, Hsinchu (TW); Li-Tao Teng, Tainan (TW)

(73) Assignee: Industrial Technology Research Institute, Hsinchu (TW)

( * ) Notice: Subject to any disclaimer, the term of this patent is extended or adjusted under 35 U.S.C. 154(b) by 233 days.

(21) Appl. No.: 15/393,265

(22) Filed: Dec. 29, 2016

(65) Prior Publication Data

US 2018/0188220 A1    Jul. 5, 2018

(51) Int. Cl.
  *G01N 33/00* (2006.01)
  *G01N 27/12* (2006.01)
  *B81B 7/00* (2006.01)

(52) U.S. Cl.
  CPC ....... *G01N 33/0073* (2013.01); *B81B 7/0096* (2013.01); *G01N 27/123* (2013.01); *G01N 27/128* (2013.01)

(58) Field of Classification Search
  CPC ............. G01N 33/0073; G01N 27/123; G01N 27/128; B81B 7/0096
  See application file for complete search history.

(56) References Cited

U.S. PATENT DOCUMENTS 7,104,113 B2    9/2006    Zribi et al.
8,640,552 B2    2/2014    Qasimi et al.
(Continued)

FOREIGN PATENT DOCUMENTS

CN    101300481    11/2008
CN    101360991    2/2009
(Continued)

OTHER PUBLICATIONS

S. Mendoza-Acevedo et al., "Design considerations for monolithic integration of a micro hotplate temperature controller in a MEMS gas sensor", Electrical Engineering,Computing Science and Automatic Control,CCE,2009 6th International Conference on, Jan. 10-13, 2009, 1~5.
(Continued)

*Primary Examiner* — Blake A Tankersley
(74) *Attorney, Agent, or Firm* — JCIPRNET

(57) ABSTRACT

A MEMS apparatus for thermal energy control including a sensor and an IC chip is provided. The sensor includes a heating device for heating a sensing element and a detecting device for detecting a physical quantity. The IC chip includes a memory unit for storing a target value of the sensing element and a data processing unit for convert the physical quantity to a converted value, where a gap value is defined by subtracting the converted value from the target value. Besides, a control unit of the IC chip sets a parameter value according to the gap value, and a driving unit adjusts a quantity of thermal energy generated by the heating device according to the parameter value to reduce heating time and frequency of the heating device thereby reducing electrical power consumption. The MEMS apparatus is applicable to MEMS sensors requiring controlled operating temperature, such as a gas sensor.

16 Claims, 7 Drawing Sheets

(56) References Cited

U.S. PATENT DOCUMENTS

| | | | |
|---|---|---|---|
| 9,279,782 B2 | 3/2016 | Chou et al. | |
| 2006/0154401 A1* | 7/2006 | Gardner | G01N 27/128 438/53 |
| 2012/0161253 A1 | 6/2012 | Hsieh et al. | |
| 2012/0297860 A1 | 11/2012 | Izawa et al. | |

FOREIGN PATENT DOCUMENTS

| | | |
|---|---|---|
| CN | 101889201 | 11/2010 |
| CN | 101975804 | 2/2011 |
| CN | 102095766 | 6/2011 |
| CN | 102681564 | 9/2012 |
| CN | 104034759 | 9/2014 |
| CN | 204154677 | 2/2015 |
| CN | 104807855 | 7/2015 |
| CN | 106053546 | 10/2016 |
| KR | 20160069944 | 6/2016 |
| TW | 200521437 | 7/2005 |
| TW | I557527 | 11/2016 |

OTHER PUBLICATIONS

V. Garofalo et al., "Mixed signal temperature control circuit for on-chip CMOS gas sensor", International Semiconductor Conference, Oct. 12-14, 2009, 495~498.

O. Leman et al., "System-level design of a readout circuit with thermostatic control for a MEMS pellistor sensor", Design, Test, Integration and Packaging of MEMS/MOEMS(DTIP), 2015 Symposium on, Apr. 27-30, 2015, 1~6.

Jian-Wei Gong et al., "Temperature feedback control for improving the stability of a semiconductor-metal-oxide (SMO) gas sensor", IEEE Sensors Journal, Feb. 2006, 139~145.

\* cited by examiner

MICRO-ELECTROMECHANICAL APPARATUS FOR THERMAL ENERGY CONTROL

TECHNICAL FIELD

The present disclosure relates to a micro-electromechanical (MEMS) apparatus, and more particularly, to a MEMS apparatus for thermal energy control.

BACKGROUND

The increasing popularity of smart micro mobile devices in daily life is closely related to the developments in the field of APP application programs in recent years. APP application programs can achieve smart interactive functions mainly because of the continuous evolution in sensing technology for human-computer interaction with the environment. By adding various sensors in the smart micro mobile device, environmental sensing information can be promptly provided for users to accomplish diverse life applications. Among all types of sensors, development of a MEMS gas sensor is by far the most compelling.

A sensing method used in a present MEMS gas sensor is to apply different electrical voltages to a heater so the heater can heat a sensing material thereby allowing the sensing material to reach preset operating temperatures of different gases. However, when a temperature of the sensing material changes due to external environment factors or other factors and the sensing material is therefore unable to operate at an optimal operating temperature, any types of the gas to be measured can affect output of the sensing material as the result. Therefore, it is unable to clearly recognize what type of the gases and a concentration thereof which induces the change in a sensing signal. In general, the electrical voltage is applied to the heater for a constant period of time to ensure that the temperature of the sensing material can reach the preset operating temperature and maintain constantly at the preset operating temperature. Yet, in the process of driving the heater to heat the sensing material, there may still be a difference between the preset operating temperature and the actual operating temperature. As such, although the aforementioned method can maintain the actual operating temperature at constant level, the preset operating temperature will not always be equal to the actual operating temperature. In addition, because the approach of providing the electrical voltage for the constant period of time to drive the heater can also provide excess heat, electrical power consumption of the MEMS gas sensor cannot be effectively reduced.

SUMMARY

The present disclosure is directed to a MEMS apparatus capable of improving a sensing accuracy while reducing electrical power consumption.

The present disclosure provides a MEMS apparatus, which includes a sensor and an IC chip. The sensor includes a sensing element, a heating device and at least one detecting device. The IC chip includes a memory unit, a data processing unit, a control unit and a driving unit. The heating device is configured to heat the heating device, the at least one detecting device is configured to detect at least one physical quantity, and the memory unit stores at least one target value. The data processing unit is adapted to convert the at least one physical quantity to at least one converted value, and at least one gap value is defined by subtracting the at least one converted value from the at least one target value. The control unit sets at least one parameter value according to at least one gap value, and the driving unit adjusts a quantity of thermal energy generated by the heating device according to the at least one parameter value.

The present disclosure further provides a MEMS apparatus, which includes a sensor and an IC chip. The sensor includes a sensing element, a heating device and at least one detecting device. The IC chip includes a memory unit, a data processing unit, a control unit and a driving unit. The heating device is configured to heat the heating device, and the at least one detecting device is configured to detect at least one physical quantity. The at least one detecting device is a power meter, and the at least one physical quantity is a power of the heating device. The memory unit stores at least one target value of the sensing element. The data processing unit is adapted to convert the at least one physical quantity to at least one converted value, and at least one gap value is defined by subtracting the at least one converted value from the at least one target value. The control unit sets at least one parameter value according to at least one gap value, and the driving unit adjusts a quantity of thermal energy generated by the heating device according to the at least one parameter value. The driving unit increases the quantity of thermal energy generated by the heating device according to the at least one parameter value when the at least one gap value is greater than zero. The driving unit decreases the quantity of thermal energy generated by the heating device according to the at least one parameter value when the at least one gap value is less than zero. The at least one parameter value includes an electrical voltage and a time, and the control unit is adapted to adjust the electrical voltage and the time according to a Joule heat equation. The Joule heat equation includes a first difference of thermal energy, a first electrical resistance value and a first electrical voltage value.

The present disclosure further provides a MEMS apparatus for sensing a gas concentration. The MEMS apparatus includes a sensor and an IC chip. The sensor includes a sensing element, a heating device and at least one detecting device. The IC chip includes a memory unit, a data processing unit, a control unit and a driving unit. The sensing element is a gas sensing layer. The heating device is configured to heat the heating device, and the at least one detecting device is configured to detect at least one physical quantity. The at least one detecting device is a power meter, and the at least one physical quantity is a power of the heating device. The power meter has a first electrical resistance value and a first electrical voltage value. The memory unit stores at least one target value of the sensing element. The data processing unit is adapted to convert the at least one physical quantity to at least one converted value, and at least one gap value is defined by subtracting the at least one converted value from the at least one target value. The at least one gap value is a first difference of thermal energy. The control unit sets at least one parameter value according to at least one gap value, and the driving unit adjusts a quantity of thermal energy generated by the heating device according to the at least one parameter value. The at least one parameter value includes an electrical voltage and a time. The control unit is adapted to adjust the electrical voltage and the time according to a Joule heat equation. The Joule heat equation includes the first difference of thermal energy, a first electrical resistance value and a first electrical voltage value.

The present disclosure further provides a MEMS apparatus for sensing a gas concentration. The MEMS apparatus includes a sensor and an IC chip. The sensor includes a sensing element, a heating device and at least one detecting device. The sensing element includes a gas sensing layer, and the heating device is configured to heat the sensing element. The at least one detecting device is configured to detect at least one physical quantity. The at least one detecting device includes a power meter. The power meter and the heating device are electrically connected in series, the power meter and the heating device are electrically connected to the IC chip respectively. An electrical resistance value of the power meter is less than an electrical resistance value of the heating device. A minimum distance from the power meter to the heating device is greater than a minimum distance from the sensing element to the heating device.

Based on the above, in the MEMS apparatus provided by embodiments of the present disclosure, because the driving device can adjust the quantity of thermal energy generated by the heating device according to the at least one physical quantity detected by the at least one detecting device, the heating device is able to provide the quantity of thermal energy for ensuring that the sensing element can indeed reach the preset operating temperature. Therefore, the MEMS apparatus is provided with higher sensing accuracy. In addition, the driving device also adjusts the quantity of thermal energy generated by the heating device according to the at least one gap value defined by subtracting the at least one converted value from the at least one target value. In this way, while the heating device is providing thermal energy so the sensing element can reach the preset operating temperature, the quantity of thermal energy generated by the heating device can be precisely controlled. Given that the heater can be driven without constantly providing electrical power for the fixed period of time, the MEMS apparatus provided by the embodiments of the present disclosure can effectively reduce electrical power consumption.

To make the above features and advantages of the present disclosure more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION

Figure 1A:
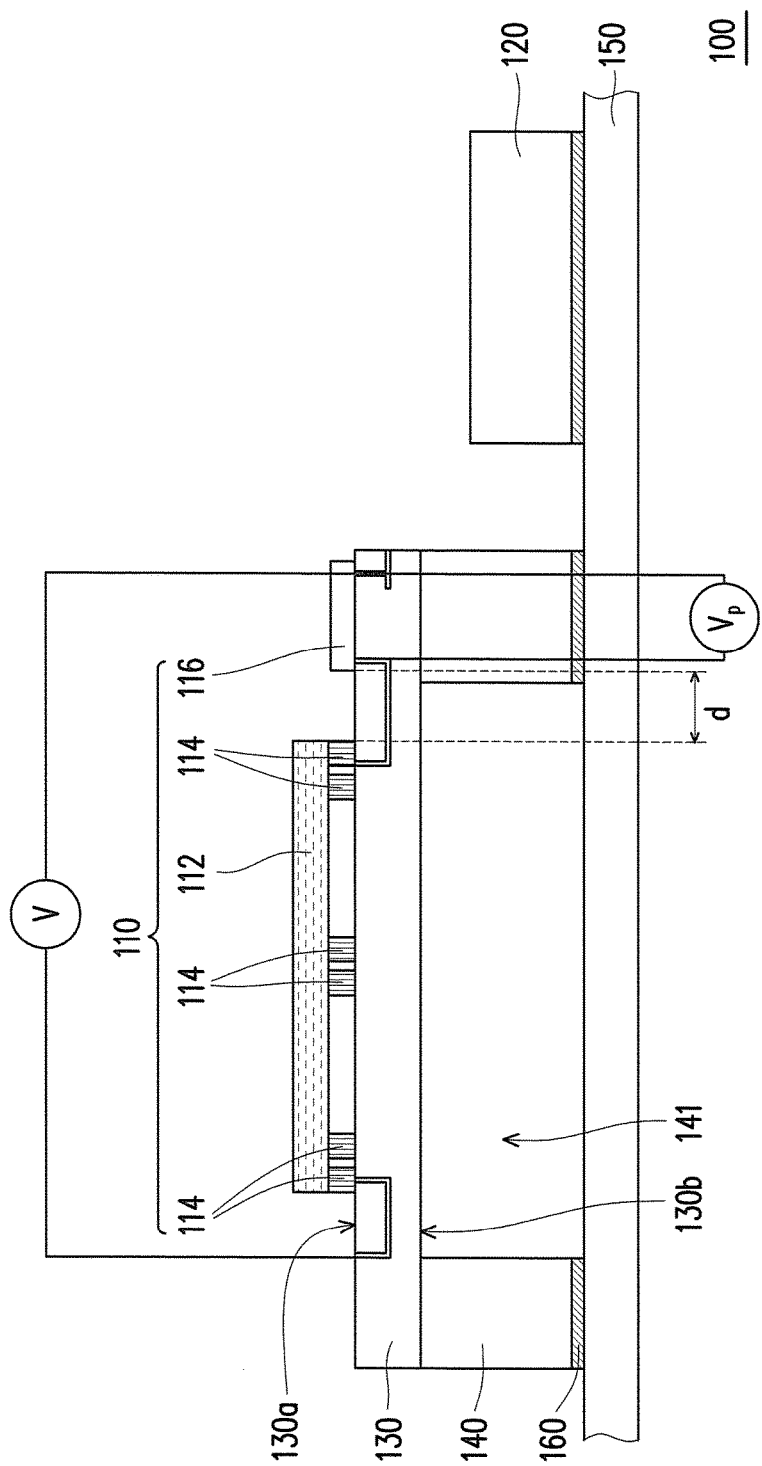
FIG. 1A is a cross-sectional view of a MEMS apparatus in the first embodiment of the present disclosure.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

FIG. 1A is a cross-sectional view of a MEMS apparatus in the first embodiment of the present disclosure. Referring to FIG. 1 in the present embodiment, a MEMS apparatus 100 is applicable to an environmental sensor, and configured to detect environmental characteristics such as gas or air quality in human environment. For instance, the MEMS apparatus 100 is adapted to sense a gas concentration or a gas-related characteristic. The MEMS apparatus 100 includes a sensor 110 and an IC chip 120, and the sensor 110 includes a sensing element 112, a heating device 114 and at least one detecting device 116. Specifically, the MEMS apparatus 100 of the present embodiment further includes a thin film 130, a base 140 and a substrate 150. The base 140 and the IC chip 120 are bonded onto the substrate 150 by a bonding layer 160, and the base 140 includes an empty space 141. In addition, the thin film 130 is disposed on the base 140, and the thin film 130 fully covers the empty space 141, for example. In other embodiment not illustrated, the thin film 130 may also partially cover the empty space so a part of the empty space is exposed in order to reduce thermal energy dissipated through the thin film, but the present disclosure is not limited thereto. In the present embodiment, the base 140 may be made of silicon materials, other semiconductor materials or glass materials, and a material of the thin film 130 may be selected from suitable materials such as silicon nitride ($Si_3N_4$), silicon dioxide ($SiO2$) and the like.

In the present embodiment, the thin film 130 has a first surface 130a and a second surface 130b opposite to the first surface 130a. The thin film 130 connects the base 140 with a part of the second surface 130b and covers the empty space 141 with another part of the second surface 130b. Further, the heating device 114 is disposed on the first surface 130a of the thin film 130. In the present embodiment, the thin film 130 may be, for example, a multi-layer or single-layer thin film, and the number of layers included by the thin film is not particularly limited by the present disclosure. Also, the thin film 130 may be made by, for example, MEMS thin film deposition processes. In addition, the heating device 114 is, for example, a heating coil made by materials, such as platinum (Pt), titanium (Ti) or tungsten (W). With electrical current being conducted through, the heating device 114 can generate thermal energy.

In the present embodiment, the sensing element 112 is disposed above the heating device 114, and the heating device 114 is disposed between the sensing element 112 and the thin film 130, for example. Specifically, the MEMS apparatus 100 is, for example, a MEMS gas sensing apparatus, and the sensing element 112 is, for example, a gas sensing layer. The sensing element 112 is in contact with the heating device 114, and the heating device 114 is configured to heat the sensing element 112. In the present embodiment, the sensing element 112, based on different types of the nano-catalysts contained therein, can sense different gases. In general, an electrical resistance value of the sensing element 112 changes according to changes in concentration of the absorbed target gas. Therefore, with observation on changes in an electrical current inputted to the sensing element 112, changes in the electrical resistance of the sensing element 112 may then be obtained through conversion so as to obtain changes in concentration of the target gas around the MEMS apparatus 100. The heating device 114 is adapted to heat the sensing element 112 to keep the sensing element 112 at a predetermined level of temperature. Accordingly, when the concentration of the target gas changes, the electrical resistance value of the sensing element 112 also changes accordingly.

In the present embodiment, the IC chip 120 is electrically coupled to the sensing element 112, the heating device 114 and the at least one detecting device 116 respectively. The at least one detecting device 116 is configured to detect at least one physical quantity. Specifically, the at least one detecting device 116 is, for example, a power meter, and the at least one physical quantity is a power $P_h$ of the heating device 114. Generally, the power meter detects the power $P_h$ of the heating device 114 through the following equation:

$$P_h = \left(\frac{V_p}{R_p}\right) \cdot V \qquad (1)$$

Herein, $V_p$ represents an electrical voltage value across the power meter when the heating device 114 is heated, which can be obtained through measurement. $R_p$ is an electrical resistance value of the power meter, which is known value. V represents an electrical voltage difference applied to the power meter and the heating device 114 by the system, which is a given value of a power supply and also a known value. In the present embodiment, the power meter is, for example, an electrical resistance device. The power meter and the heating device 114 are electrically connected in series, and an electrical resistance value of the power meter is less than an electrical resistance value of the heating device 114.

In the present embodiment, the power meter (the at least one detecting device 116) is disposed on the first surface 130a of the thin film 130, and a minimum distance from the power meter to the heating device 114 (e.g., a distance D illustrated in FIG. 1A) is greater than a minimum distance from the sensing element 112 to the heating device 114. In detail, the power meter is disposed at a position far way from the heating device 114 but not limited to be a specific position on the thin film 130. As such, the electrical resistance value of the power meter will not be affected by a high temperature so the accuracy of the power meter during measurement can be ensured. In some embodiments, the power meter may be also disposed on other positions of the MEMS apparatus 100 (e.g., on the substrate 150). In addition, in order to obtain the power $P_h$ of the heating device 114 by using the equation (1) in the present embodiment, the power meter (the at least one detecting device 116) and the heating device 114 need to be electrically connected in series, and the electrical resistance value $R_p$ of the power meter needs to be less than the electrical resistance value $R_h$ of the heating device 114.

Figure 1B:
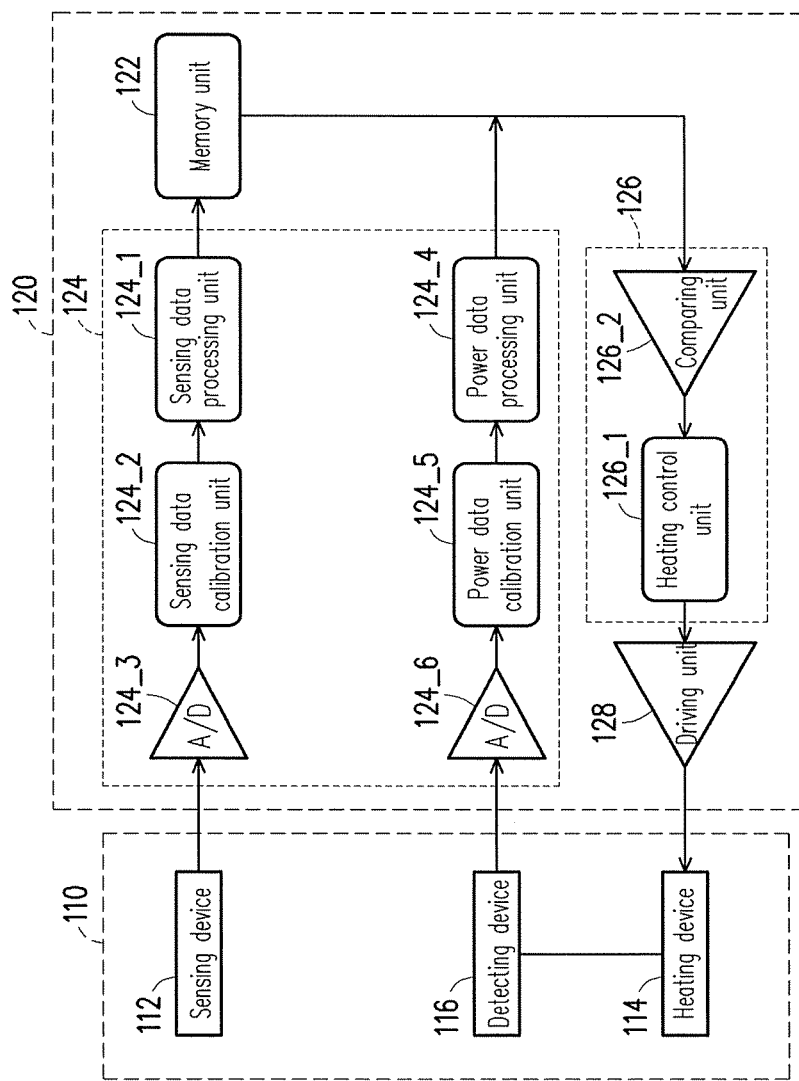
FIG. 1B is a schematic diagram of a sensor and an IC chip in the first embodiment of the present disclosure.

FIG. 1B is a schematic diagram of a sensor and an IC chip in the first embodiment of the present disclosure. Referring to FIG. 1A and FIG. 1B together, in the present embodiment, the IC chip 120 includes a memory unit 122, a data processing unit 124, a control unit 126 and a driving unit 128, which are electrically coupled. The memory unit 122 is configured to store at least one target value of the sensing element 112, and the at least one target value is a predetermined quantity value of thermal energy adapted to heat the sensing element 112 for a concentration detection on the target gas, for example. The data processing unit 124 is adapted to convert the at least one physical quantity such as the power $P_h$ of the heating device 114 detected by the said power meter (the at least one detecting device 116) to at least one converted value such as a quantity of thermal energy of the heating device 114.

Specifically, the data processing unit 124 includes a sensing data processing unit 124_1, a sensing data calibration unit 124_2, an analog-to-digital converting unit 124_3, a power data processing unit 124_4, a power data calibration unit 124_5 and an analog-to-digital converting unit 124_6. After an electrical resistance signal of the sensing element 112 is, for example, converted to a digital signal through the analog-to-digital converting unit 124_3, a signal offset in such digital signal is calibrated by the data calibration unit 124_2, and then the resultant signal is transmitted to the sensing data processing unit 124_1 for sensing changes in concentration of the target gas. In addition, after an electrical signal (the electrical voltage difference) detected by the power meter is, for example, converted to a digital signal through the analog-to-digital converting unit 124_6, a signal offset in such digital signal is calibrated by the power data calibration unit 124_5, and then the resultant signal is transmitted to the power data processing unit 1244.

In the present embodiment, the power data processing unit 124_4 obtains the power $P_h$ of the heating device 114 through the equation (1), for example. In addition, the power data processing unit 124_4 obtains the quantity value of thermal energy actually outputted by the heating device 114 (the at least one converted value) according to the power $P_h$ and a heating time t of the heating device 114. Specifically, at least one gap value is defined by subtracting the at least one converted value from the at least one target value. The at least one gap value is, for example, a first difference of thermal energy $\Delta Q_1$ obtained by subtracting the quantity value of thermal energy (the converted value) actually outputted by the heating device 114 from the predetermined quantity value of thermal energy (target value).

In the present embodiment, the control unit 126 sets at least one parameter value according to the at least one gap value (the first difference of thermal energy $\Delta Q_1$). According to the at least one parameter value, the driving unit 128 drives the heating device 114 to adjusts the quantity of thermal energy generated by the heating device 114. Specifically, the control unit 126 includes a heating control unit 126_1 and a comparing unit 126_2. The comparing unit 1262 receives signals provided by the power data processing unit 124_4 and the memory unit 122, and determines whether the quantity value of thermal energy actually outputted by the heating device 114 reaches the predetermined quantity value of thermal energy. If the quantity value of thermal energy actually outputted by the heating device 114 does not reach the predetermined quantity value of thermal energy, the heating control unit 126_1 controls the driving unit 128 to drive the heating device 114 for heating so the first difference of thermal energy $\Delta Q_1$ can be compensated. In detail, when the first difference of thermal energy $\Delta Q_1$ (the at least one gap value) is greater than zero, it means that the quantity value of thermal energy actually outputted does not reach the predetermined quantity value of thermal energy. In this case, the driving unit 128 drives the heating device 114 to increase the quantity of thermal energy generated by the heating device 114 according to the at least one parameter value. In addition, when the first difference of thermal energy $\Delta Q_1$ (the at least one gap value) is less than zero, it means that the quantity value of thermal energy actually outputted exceeds the predetermined quantity value of thermal energy. In this case, the driving unit 128 drives the heating device 114 to decrease the quantity of thermal energy generated by the heating device 114 according to the at least one parameter value.

In detail, the control unit 126 (e.g., the heating control unit 126_1) sets the at least one parameter value according to the first difference of thermal energy $\Delta Q_1$. The at least one parameter value includes, for example, an electrical voltage V and a time t. The control unit 126 is adapted to adjust the electrical voltage V and the time t according to a Joule heat equation, and the Joule heat equation includes the first difference of thermal energy $\Delta Q_1$, a first electrical resistance value $R_p$ (i.e., the electrical resistance value $R_p$ of the power meter) and a first electrical voltage value $V_p$ (i.e., the electrical voltage value $V_p$ across the power meter when the heating device 114 is heated). The Joule heat equation is provided as follows.

$$\Delta Q_1 = P_h \times t = \left(\frac{V}{R_p}\right) \cdot \int_0^t V_p(t) \cdot dt \qquad (2)$$

Specifically, the MEMS apparatus 100 can set the electrical voltage difference (the electrical voltage V) applied to the power meter and the heating device 114 by the system and/or can set the heating time t of the heating device 114 for heating as driven by the system to meet the Joule heat equation (equation (2)), so as to adjust the quantity of thermal energy generated by the heating device 114 to thereby compensate the first difference of thermal energy $\Delta Q_1$. In this way, the quantity of thermal energy generated by the heating device 114 can be precisely controlled.

In addition, the memory unit 122 is also adapted to store at least one data of the electrical voltage V and the time t that are optimized in experiment for compensation of the first difference of thermal energy $\Delta Q_1$. It means that the capability of the at least one data of the electrical voltage V and the time t that are actually used in experiment for enabling the heating device 114 to precisely compensate the first difference of thermal energy $\Delta Q_1$ has been experimentally verified. With regard to the first difference of thermal energy $\Delta Q_1$, the control unit 126 can directly adopt the at least one data of the electrical voltage V and the time t that are optimized to rapidly compensate the first difference of thermal energy $\Delta Q_1$. Specifically, given that the heating device 114 can be driven without constantly providing electrical power for the constant period of time, the MEMS apparatus 100 in the first embodiment of the present disclosure can effectively reduce electrical power consumption.

Figure 2A:
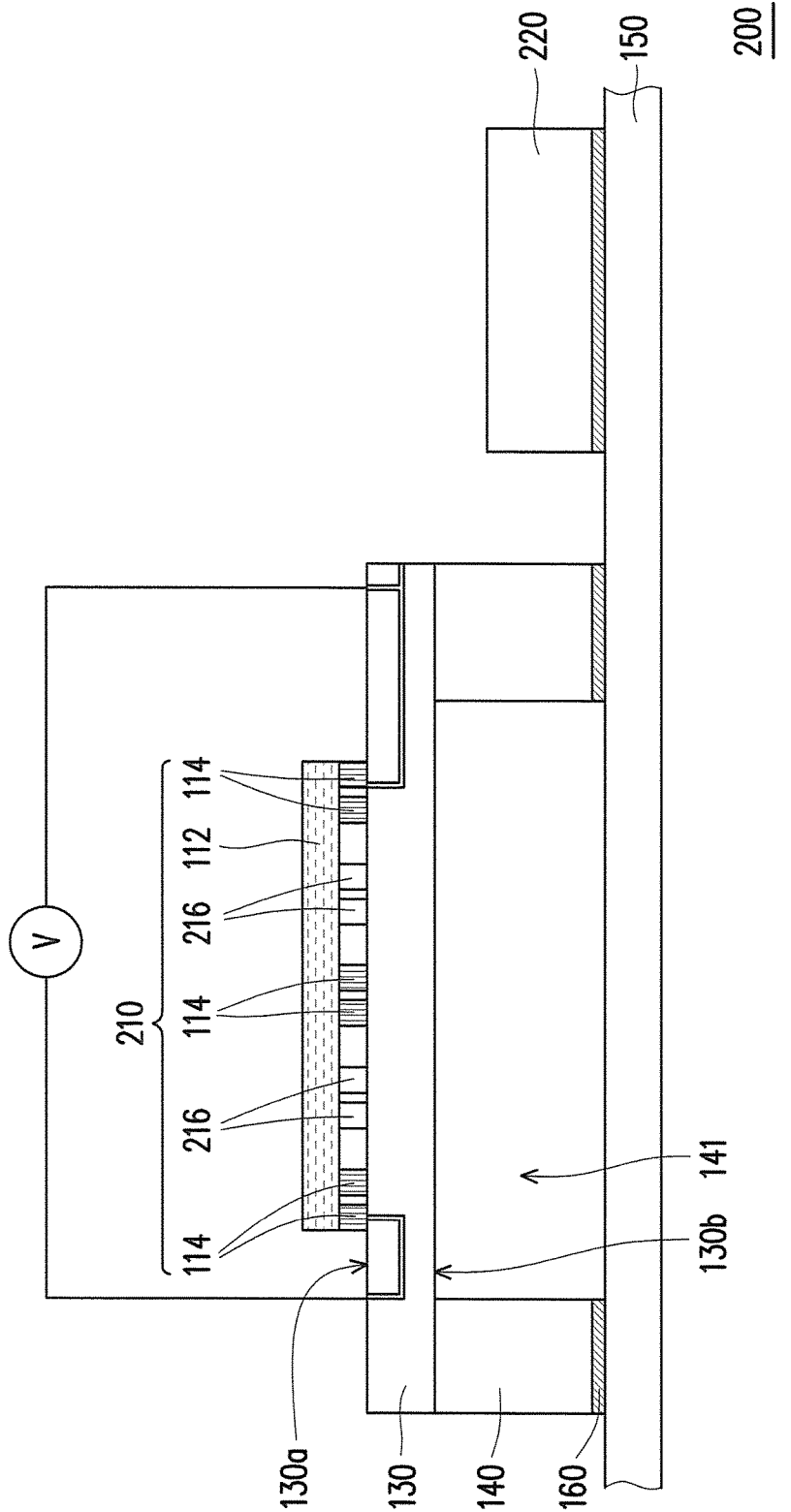
FIG. 2A is a cross-sectional view of a MEMS apparatus in the second embodiment of the present disclosure.
Figure 2B:
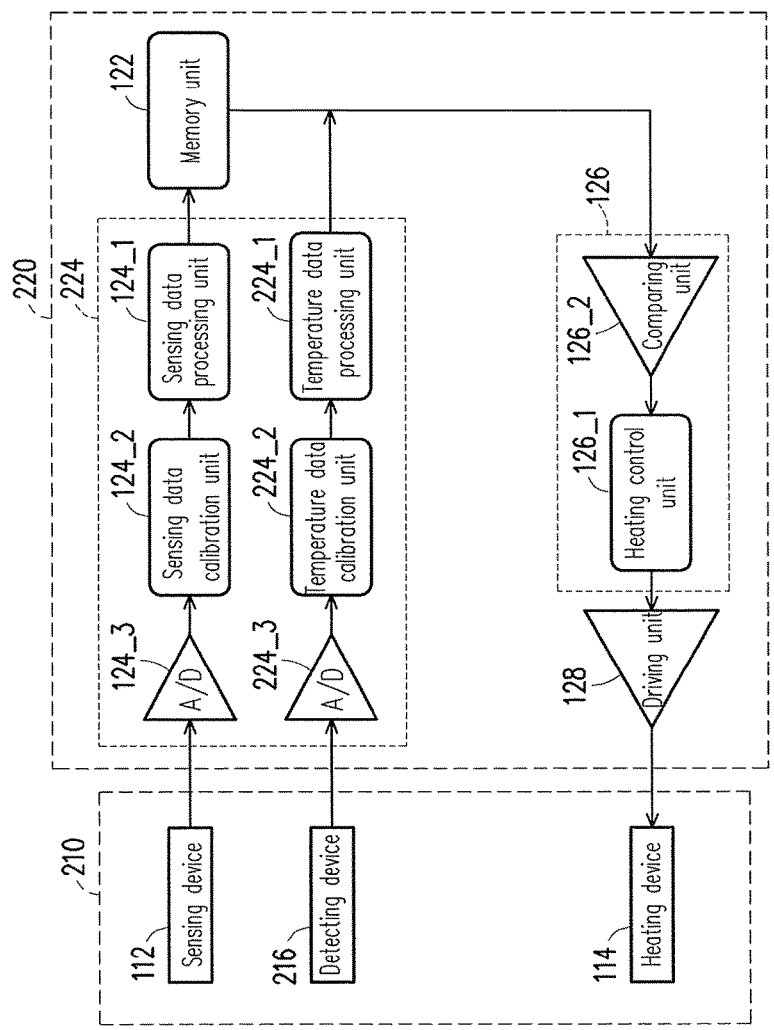
FIG. 2B is a schematic diagram of a sensor and an IC chip in the second embodiment of the present disclosure.

FIG. 2A is a cross-sectional view of a MEMS apparatus in the second embodiment of the present disclosure, and FIG. 2B is a schematic diagram of a sensor and an IC chip in the second embodiment of the present disclosure. With reference to FIG. 2A, a MEMS apparatus 200 in the embodiment of FIG. 2A is similar to the MEMS apparatus 100 in the embodiment of FIG. 1A with the following difference. A sensor 210 of the MEMS apparatus 200 includes at least one detecting device 216, and the at least one detecting device 216 is, for example, a thermometer. The thermometer (the at least one detecting device 216) is disposed between the heating device 114 and the sensing element 112. In this way, thermal energy generated by the heating device 114 does not dissipate and the thermometer can precisely detect a temperature of the sensing element 112. In addition, with reference to FIG. 2B, in the present embodiment, a data processing unit 224 of an IC chip 220 further includes a temperature data processing unit 224_1, a temperature data calibration unit 224_2 and an analog-to-digital converting unit 224_3 in addition to the sensing data processing unit 124_1, the sensing data calibration unit 124_2 and the analog-to-digital converting unit 124_3. After an electrical signal of the thermometer is, for example, converted to a digital signal through the analog-to-digital converting unit 224_3, a signal offset in such digital signal is calibrated by the temperature data calibration unit 224_2, and then the resultant signal is transmitted to the temperature data processing unit 224_1.

In the present embodiment, the data processing unit 224 is adapted to convert the electrical signal provided by the thermometer (the at least one detecting device 216) to a temperature value (at least one converted value) for a temperature difference $\Delta T$ calculation. In addition, a temperature difference $\Delta T$ (at least one gap value) is obtained by subtracting said temperature value (the at least one converted value) from a predetermined temperature (at least one target value stored by the memory unit). In the present embodiment, the control unit 126 is adapted to set at least one parameter value according to the temperature difference $\Delta T$. The at least one parameter value includes an electrical voltage V and a time t. Specifically, the control unit 126 can adjust the electrical voltage V and the time t according to at least one data corresponding to the temperature difference $\Delta T$. The at least one data is optimized from experiment and is stored in the memory unit 122. In other words, the MEMS apparatus 200 can use the at least one data from experiment to set electrical voltage V and the time t to adjust the quantity of thermal energy generated by the heating device 114 so as to rapidly and precisely compensate the temperature difference $\Delta T$. Specifically, the at least one detecting device 216 (the thermometer) of the MEMS apparatus 200 in the second embodiment of the present disclosure can detect the temperature of the sensing element 112. In addition, the MEMS apparatus 200 can obtain the temperature difference $\Delta T$ according to the detected temperature of the sensing element 112 and adjust the quantity of thermal energy generated by the heating device 114 according to the temperature difference $\Delta T$. In this way, the heating device 114 can provide thermal energy that ensures the sensing element 112 can indeed reach the predetermined operating temperature. Therefore, the MEMS apparatus 200 is provided with higher sensing accuracy. In addition, given that the heating device 114 can be driven without constantly providing electrical power, the MEMS apparatus 200 in the second embodiment of the present disclosure can effectively reduce electrical power consumption.

Figure 3A:
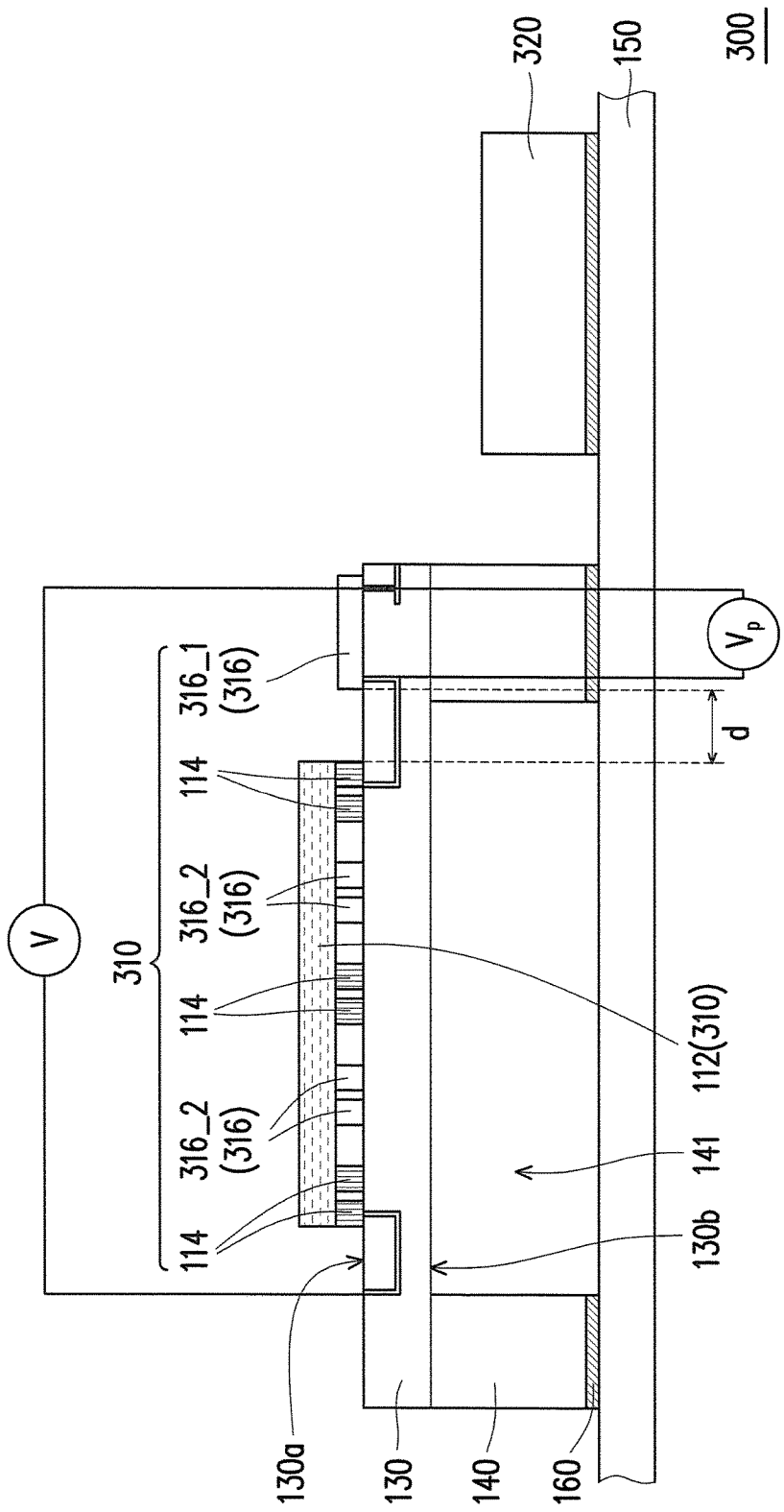
FIG. 3A is a cross-sectional view of a MEMS apparatus in the third embodiment of the present disclosure.
Figure 3B:
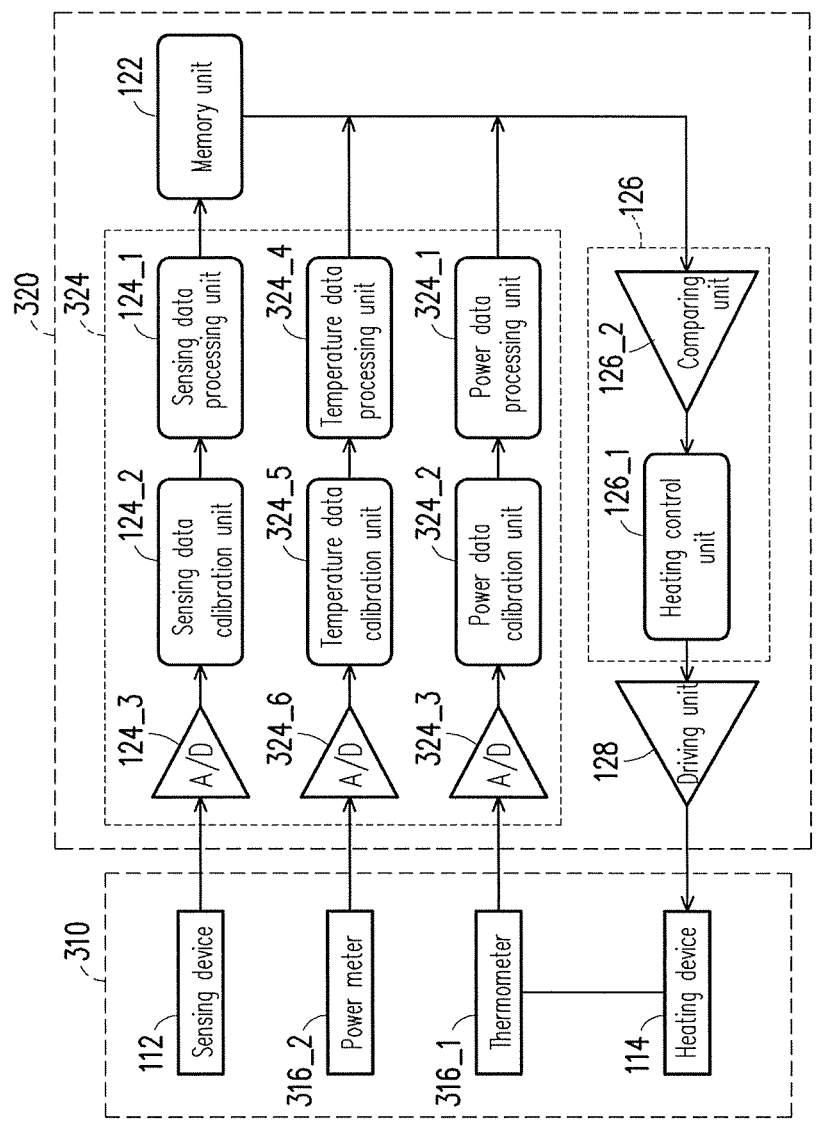
FIG. 3B is a schematic diagram of a sensor and an IC chip in the third embodiment of the present disclosure.

FIG. 3A is a cross-sectional view of a MEMS apparatus in the third embodiment of the present disclosure, and FIG. 3B is a schematic diagram of a sensor and an IC chip in the third embodiment of the present disclosure. With reference to FIG. 3A, a MEMS apparatus 300 in the embodiment of FIG. 3A is similar to the MEMS apparatus 100 in the embodiment of FIG. 1A with the following difference. A sensor 310 of the MEMS apparatus 300 includes at least one detecting device 316. The at least one detecting device 316 includes a power meter 316_1 and a thermometer 316_2. The power meter 316_1 is configured to detect a power of the heating device 114, and the thermometer 316_2 is configured to detect a temperature of the sensing element 112. In addition, by making an electrical resistance value $R_n$ of the power meter 316_1 less than an electrical resistance value $R_n$ of the heating device 114, the power meter 316_1 can obtain the power $P_h$ of the heating device 114 by using the equation (1). Further, in the present embodiment, the power meter 316_1 is similar to the at least one detecting device 116 (the power meter) in the embodiment of FIG. 1A, and the thermometer 316_2 is similar to the at least one detecting device 216 (the thermometer) in the embodiment of FIG. 2A. In addition, with reference to FIG. 3B, in the present embodiment, a data processing unit 324 of an IC chip 320 further includes a power data processing unit 324_1, a power data calibration unit 324_2, an analog-to-digital converting unit 324_3, a temperature data processing unit 324_4, a temperature data calibration unit 324_5 and an analog-to-digital converting unit 324_6 in addition to the sensing data processing unit 124_1, the sensing data calibration unit 124_2 and the analog-to-digital converting unit 124_3. Specifically, after an electrical signal of the power meter 316_1 is, for example, converted to a digital signal through the analog-to-digital converting unit 324_3, a signal offset in such digital signal is calibrated by the power data calibration unit 324_2, and then the resultant signal is transmitted to the power data processing unit 324_1. Further, after an electrical signal of the thermometer 316_2 is, for example, converted to a digital signal through the analog-to-digital converting unit 324_6, a signal offset in such digital signal is calibrated by the temperature data calibration unit 324_5, and then the resultant signal is transmitted to the temperature data processing unit 324_4.

In the present embodiment, the data processing unit 324 is adapted to convert the electrical signal provided by the power meter 316_1 to a power value to thereby obtain a quantity value of thermal energy actually outputted by the heating device 114. Further, a first difference of thermal energy $\Delta Q_1$ is obtained by subtracting the quantity value of thermal energy actually outputted by the heating device 114 from a predetermined quantity value of thermal energy. In addition, the data processing unit 324 is also adapted to convert the electrical signal provided by the thermometer 316_2 to a temperature value. Moreover, the MEMS apparatus 300 can calculate a second difference of thermal energy $\Delta Q_2$ according to the temperature value stored by the memory unit 122. The second difference of thermal energy $\Delta Q2$ can be obtained through the following equation:

$$\Delta Q_2 = m \cdot s \cdot \Delta t \quad (3)$$

Herein, m is a mass of the sensing element 112, s is a specific heat of the sensing element 112, $\Delta t$ is, for example, a temperature difference between the temperature value measured by the thermometer 316_2 and a target temperature value stored in the memory unit 122.

In the present embodiment, the control unit 126 sets at least one parameter value according to at least one gap value (the first difference of thermal energy $\Delta Q_1$ and the second difference of thermal energy $\Delta Q_2$). According to aforesaid at least one parameter value, the driving unit 128 drives the heating device 114 to adjusts the quantity of thermal energy generated by the heating device 114. Specifically, the at least one parameter value includes an electrical voltage V to be applied to the heating device 114 by the system and a heating time t of the heating device 114 for heating as driven by the system. In other words, the control unit 126 can adjust the electrical voltage V and the time t according to the first difference of thermal energy $\Delta Q_1$ and the second difference of thermal energy $\Delta Q_2$, so as to adjust quantity of thermal energy generated by the heating device 114. Specifically, the MEMS apparatus 300 in the third embodiment of the present disclosure can at least provide technical features similar to those described in the first embodiment and the second embodiment of the present disclosure. Therefore, the MEMS apparatus 300 is provided with higher sensing accuracy and capable of effectively reducing electrical power consumption. In addition, it is noted that the MEMS apparatus 300 can use both the temperature of the sensing element 112 measured by the thermometer 316_2 and the power of the heating device 114 measured by the power meter 316_1 to as the reference for the MEMS apparatus 300 to adjust thereby compensating the quantity of thermal energy generated by the heating device 114. Therefore, in comparison with the first embodiment and the second embodiment, the MEMS apparatus 300 is capable of compensating the quantity of thermal energy even more precisely while reducing frequency and time for compensating the quantity of thermal energy to thereby effectively reducing electrical power consumption.

Specifically, components including the sensing data processing unit 124_1, the sensing data calibration unit 124_2, the analog-to-digital converting units 124_3, 124_6, 224_3, 324_3 and 324_6, the power processing units 124_4 and 324_1, the power data calibration units 124_5 and 324_2, the temperature data processing units 224_1 and 324_4, the temperature data calibration units 224_2 and 324_5, the heating control unit 126_1 the comparing unit 126_2 and the driving unit 128 as described in the first embodiment, the second embodiment and the third embodiment may be implemented by hardware with computing capabilities (e.g., a chip set, a processor, etc.). For instance, aforementioned components may be implemented using a central processing unit (CPU), or other programmable microprocessors, an application specific integrated circuits (ASIC), or other similar devices, but the present disclosure is not limited to the above.

Furthermore, the memory unit 122 described in the first embodiment, the second embodiment and the third embodiment may be an embedded storage unit or an external storage unit. The embedded storage unit may be a random access memory (RAM), a read-only memory (ROM), a flash memory, a magnetic disk storage device, and so on. The external storage unit may be compact flash (CF) memory card, secure digital (SD) memory card, micro SD memory card, memory stick (MS) memory card, and so on. However, the present disclosure is not limited to the above.

Figure 4:
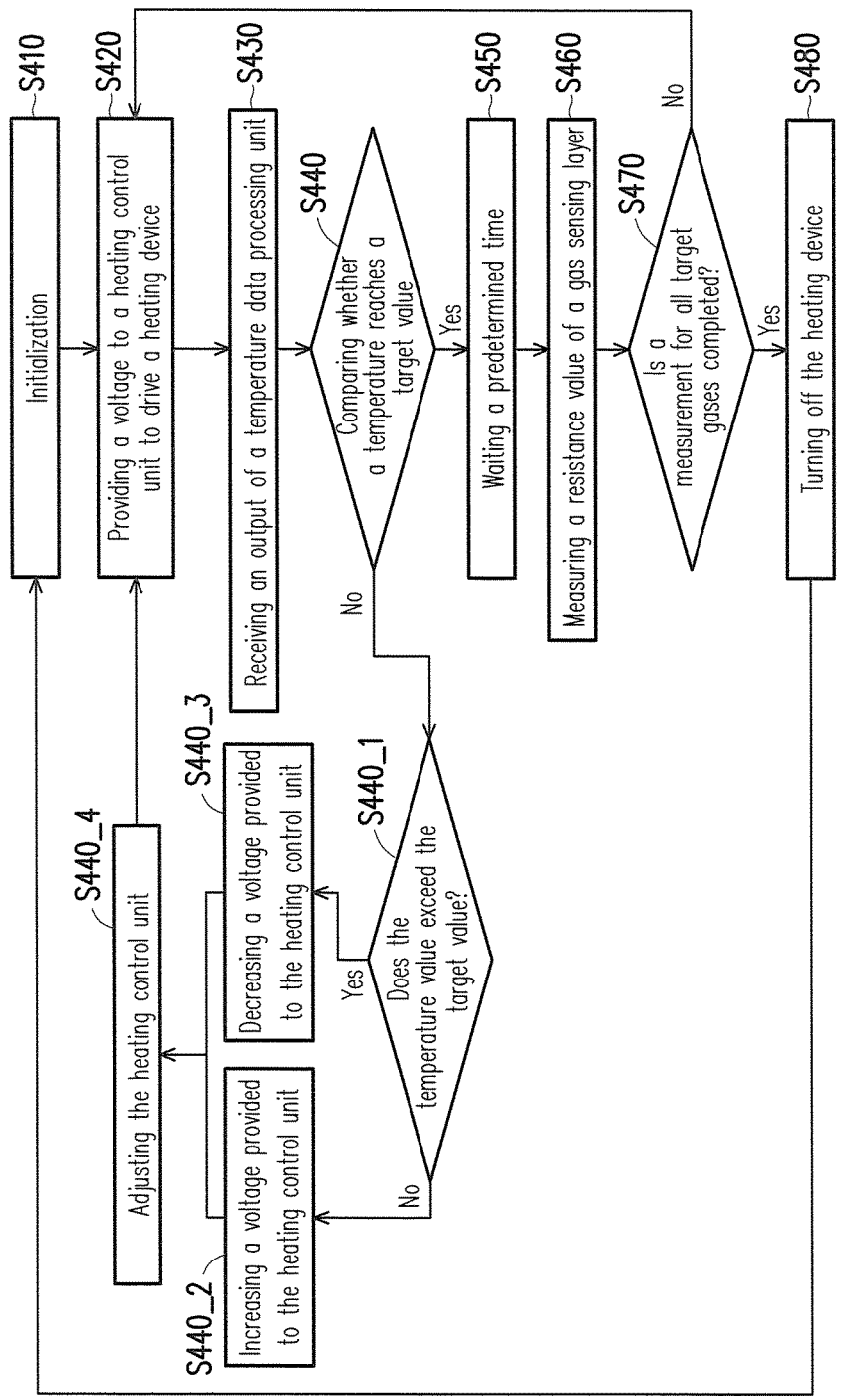
FIG. 4 is a flowchart illustrating steps in a sensing method of many kinds of gas according to an embodiment of the present disclosure.

FIG. 4 is a flowchart illustrating steps in a sensing method of multiple gases according to an embodiment of the present disclosure. With reference to FIG. 4, in the present embodiment, the gas sensing method is at least applicable to the MEMS apparatus 200 in the embodiment of FIG. 2A. The gas sensing method includes the following steps. In step S410, an initialization is performed on a MEMS apparatus. Next, in step S420, an electrical voltage is provided to a heating control unit according to a temperature setting stored in a memory unit so as to drive a heating device to heat a sensing element. It is noted that the quantity value of electrical voltage in this Step 420 is predetermined and stored in a memory. Then, in step S430, an output (e.g., a temperature of the sensing element) of a temperature data processing unit is received. Next, in step S440, it is determined whether a temperature value reaches a target value (a predetermined temperature). If the target value is not reached, it is determined whether the temperature value of the sensing element exceeds the target value in step S440_1. Specifically, when a temperature difference (at least one gap value) obtained by subtracting the temperature value from a predetermined temperature (the target value) is greater than zero, it means that the temperature value of the sensing element does not exceed the target value and also means that the temperature value of the sensing element is less than the target value. In this case, an electrical voltage provided to the heating control unit is increased to increase a quantity of thermal energy generated by the heating device in step S440_2. Further, when the temperature difference (at least one gap value) is less than zero, it means that the temperature value of the sensing element exceeds the target value and also means that the temperature value of the sensing element is greater than the target value. In this case, an electrical voltage provided to the heating control unit is decreased to decrease a quantity of thermal energy generated by the heating device in step S440_3. An increment of the electrical voltage value provided to the heating control unit or a decrement of the electrical voltage value provided to the heating control unit is obtained according to experimental data corresponding to the gap value (the temperature difference obtained by subtracting the temperature value of the sensing value from the target value). The corresponding experimental data are already stored in memory before the initialization of the MEMS apparatus is performed. Next, in step S440_4, the heating control unit adjusts the electrical voltage value and provides an updated electrical voltage. In step S420, the updated electrical voltage is provided to the heating control unit again to drive the heating device to heat the sensing element. It is noted that the quantity value of electrical voltage in this Step 420 is an updated electrical voltage.

Further, if the temperature value of the sensing element reaches the target value in step S440, after a predetermined time is waited in step S450, an electrical resistance value of a gas sensing layer (the sensing element) is measured in step S460, so as to sense a concentration of the target gas, for example. Then, it is determined whether a measurement for all target gases is completed in step S470. If the measurement for all the target gases is not yet completed, step S420 to step S460 are repeatedly performed to measure each of the target gases. If the measurement for all the target gases is completed, the process proceeds to step S480 in which the heating device is turned off. Specifically, sufficient teaching, suggestion, and implementation illustration regarding the gas sensing method in the embodiment of the present disclosure can be obtained from the embodiments of FIG. 1A through FIG. 3B, and thus related description thereof is not repeated hereinafter.

In summary, in the MEMS apparatus according to embodiments of the present disclosure, the driving device drives the heating device by providing an updated voltage for adjusting the quantity of thermal energy according to the at least one physical quantity detected by the at least one detecting device. Accordingly, the heating device can provide the precise thermal energy for the sensing element to rapidly and surely reach the preset operating temperature. Therefore, the MEMS apparatus is provided with higher sensing accuracy. In addition, the driving device also drives the heating device by providing updated voltage for adjusting the quantity of thermal energy generated by the heating device according to the at least one gap value defined by subtracting the at least one converted value from the at least one target value. In this way, while the heating device is providing thermal energy so the sensing element can reach the preset operating temperature, the quantity of thermal energy generated by the heating device can be precisely controlled. Given that the heater can be driven without constantly providing electrical power for the constant period of time, the MEMS apparatus provided by the embodiments of the present disclosure can effectively reduce electrical power consumption.

It will be apparent to those skilled in the art that various modifications and variations can be made to the disclosed embodiments. It is intended that the specification and examples be considered as exemplary only, with a true scope of the present disclosure being indicated by the following claims and their equivalents.

What is claimed is:

1. A MEMS apparatus, comprising:
   a sensor, comprising:
      a sensing element;
      a heating device configured to heat the sensing element; and
      at least one detecting device configured to detect at least one physical quantity; and
   an IC chip, comprising:
      a memory unit storing at least one target value of the sensing element;
      a data processing unit, wherein the data processing unit is adapted to convert the at least one physical quantity to at least one converted value, and at least one gap value is defined by subtracting the at least one converted value from the at least one target value;
      a control unit providing at least one parameter value according to the at least one gap value, wherein the at least one parameter value comprises an electrical voltage and time, the control unit is adapted to adjust the electrical voltage and time; and
      a driving unit adapted to drive the heating device to adjust a quantity of thermal energy generated by the heating device according to the at least one parameter value.

2. The MEMS apparatus of claim 1, wherein the at least one detecting device comprises a power meter, and the at least one physical quantity comprises a power of the heating device.

3. The MEMS apparatus of claim 2, wherein the at least one gap value comprises a first difference of thermal energy.

4. The MEMS apparatus of claim 3, wherein the control unit is adapted to adjust the electrical voltage and the time according to a Joule heat equation, and the Joule heat equation comprises the first difference of thermal energy, a first electrical resistance value and a first electrical voltage value.

5. The MEMS apparatus of claim 4, wherein the electrical voltage and the time satisfy the following equation:

$$\Delta Q_1 = \left(\frac{V}{R_p}\right) \cdot \int_0^t V_p(t) \cdot dt$$

wherein $\Delta Q_1$ is the first difference of thermal energy, V is the electrical voltage, $R_p$ is the first electrical resistance value, $V_p$ is the first electrical voltage value across the power meter when the heating device is heated, and t is the time.

6. The MEMS apparatus of claim 2, wherein a minimum distance from the power meter to the heating device is greater than a minimum distance from the sensing element to the heating device.

7. The MEMS apparatus of claim 2, wherein the power meter and the heating device are electrically connected in series, and an electrical resistance value of the power meter is less than an electrical resistance value of the heating device.

8. The MEMS apparatus of claim 1, wherein the at least one detecting device comprises a thermometer, and the at least one physical quantity comprises a temperature of the sensing element.

9. The MEMS apparatus of claim 8, wherein the at least one gap value comprises a temperature difference.

10. The MEMS apparatus of claim 9, wherein the control unit is adapted to adjust the electrical voltage and the time according to at least one data corresponding to the temperature difference, and the at least one data is stored in the memory unit.

11. The MEMS apparatus of claim 8, wherein the thermometer is disposed between the heating device and the sensing element.

12. A MEMS apparatus, comprising:
a sensor, comprising:
   a sensing element;
   a heating device configured to heat the sensing element; and
   at least one detecting device configured to detect at least one physical quantity; and
an IC chip, comprising:
   a memory unit storing at least one target value of the sensing element;
   a data processing unit, wherein the data processing unit is adapted to convert the at least one physical quantity to at least one converted value, and at least one gap value is defined by subtracting the at least one converted value from the at least one target value;
   a control unit providing at least one parameter value according to the at least one gap value; and
   a driving unit adapted to drive the heating device to adjust a quantity of thermal energy generated by the heating device according to the at least one parameter value, wherein the driving unit increases the quantity of thermal energy generated by the heating device according to the at least one parameter value when the at least one gap value is greater than zero, the driving unit decreases the quantity of thermal energy generated by the heating device according to the at least one parameter value when the at least one gap value is less than zero, the at least one parameter value comprises an electrical voltage and a time, and the control unit is adapted to adjust the electrical voltage and the time according to a Joule heat equation comprising a first difference of thermal energy, a first electrical resistance value and a first electrical voltage value.

13. The MEMS apparatus of claim 12, wherein the at least one detecting device comprises a power meter, and the at least one physical quantity comprises a power of the heating device.

14. The MEMS apparatus of claim 13, wherein the at least one gap value comprises the first difference of thermal energy, the power meter has the first electrical resistance value and the first electrical voltage value, and the electrical voltage and the time satisfy the following equation:

$$\Delta Q_1 = \left(\frac{V}{R_p}\right) \cdot \int_0^t V_p(t) \cdot dt$$

wherein $\Delta Q_1$ is the first difference of thermal energy, V is the electrical voltage, $R_p$ is the first electrical resistance value, $V_p$ is the first electrical voltage value across the power meter when the heating device is heated, and t is the time.

15. A MEMS apparatus, being adapted to sense a gas concentration, the MEMS apparatus comprising:
a sensor, comprising:
   a sensing element comprising a gas sensing layer;
   a heating device configured to heat the sensing element; and
   at least one detecting device configured to detect at least one physical quantity, wherein the at least one detecting device comprises a power meter, the at least one physical quantity comprises a power of the heating device, and the power meter has a first electrical resistance value and a first electrical voltage value that is defined as an electrical voltage value across the power meter when the heating device is heated; and
an IC chip, comprising:
   a memory unit storing at least one target value of the sensing element;
   a data processing unit, wherein the data processing unit is adapted to convert the at least one physical quantity to at least one converted value, at least one gap value is defined by subtracting the at least one converted value from the at least one target value, and the at least one gap value comprises a first difference of thermal energy;
   a control unit providing at least one parameter value according to the at least one gap value; and
   a driving unit adapted to drive the heating device to adjust a quantity of thermal energy generated by the heating device according to the at least one parameter value, wherein the at least one parameter value comprises an electrical voltage and a time, the control unit is adapted to adjust the electrical voltage and the time according to a Joule heat equation comprising a first difference of thermal energy, a first electrical resistance value and a first electrical voltage value.

16. A MEMS apparatus, being adapted to sense a gas concentration, the MEMS apparatus comprising:
a sensor, comprising:
a sensing element comprising a gas sensing layer;
a heating device configured to heat the sensing element; and
at least one detecting device configured to detect at least one physical quantity, wherein the at least one detecting device comprises a power meter; and
an IC chip; and
wherein the power meter and the heating device are electrically connected in series, the power meter and the heating device are electrically connected to the IC chip respectively, an electrical resistance value of the power meter is less than an electrical resistance value of the heating device, a minimum distance from the power meter to the heating device is greater than a minimum distance from the sensing element to the heating device.

* * * * *